United States Patent
Eggert

(10) Patent No.: US 10,125,155 B2
(45) Date of Patent: Nov. 13, 2018

(54) SILANE MODIFIED FORMAMIDES

(71) Applicant: Covestro Deutschland AG, Leverkusen (DE)

(72) Inventor: Christoph Eggert, Köln (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 15/112,308

(22) PCT Filed: Jan. 26, 2015

(86) PCT No.: PCT/EP2015/051445
§ 371 (c)(1),
(2) Date: Jul. 18, 2016

(87) PCT Pub. No.: WO2015/113923
PCT Pub. Date: Aug. 6, 2015

(65) Prior Publication Data
US 2016/0340371 A1  Nov. 24, 2016

(30) Foreign Application Priority Data
Jan. 31, 2014  (EP) .................................. 14153502

(51) Int. Cl.
| | | |
|---|---|---|
| *C07F 7/18* | (2006.01) | |
| *C08G 18/48* | (2006.01) | |
| *C08G 18/62* | (2006.01) | |
| *C08G 18/71* | (2006.01) | |
| *C08G 18/73* | (2006.01) | |
| *C08G 18/75* | (2006.01) | |
| *C08G 18/76* | (2006.01) | |
| *C08G 18/28* | (2006.01) | |
| *C09J 175/04* | (2006.01) | |
| *C08G 18/10* | (2006.01) | |
| *C09D 183/16* | (2006.01) | |
| *C09J 183/16* | (2006.01) | |

(52) U.S. Cl.
CPC ............ *C07F 7/1804* (2013.01); *C07F 7/184* (2013.01); *C07F 7/1836* (2013.01); *C07F 7/1888* (2013.01); *C08G 18/10* (2013.01); *C08G 18/289* (2013.01); *C08G 18/4825* (2013.01); *C08G 18/6216* (2013.01); *C08G 18/718* (2013.01); *C08G 18/73* (2013.01); *C08G 18/755* (2013.01); *C08G 18/7621* (2013.01); *C09D 183/16* (2013.01); *C09J 175/04* (2013.01); *C09J 183/16* (2013.01)

(58) Field of Classification Search
CPC ......... C07F 7/18; C08G 18/10; C09D 183/16; C09J 175/04; C09J 183/16
USPC ......................................................... 556/414
See application file for complete search history.

(56) References Cited

U.S. PATENT DOCUMENTS

| | | | |
|---|---|---|---|
| 3,640,967 | A | 2/1972 | König |
| 4,218,543 | A | 8/1980 | Weber et al. |
| 4,499,150 | A | 2/1985 | Dowbenko et al. |
| 6,730,768 | B2 | 5/2004 | Heidbreder et al. |
| 2012/0245241 | A1 | 9/2012 | Peiffer et al. |

FOREIGN PATENT DOCUMENTS

| | | | |
|---|---|---|---|
| DE | 1770245 | A1 | 10/1971 |
| DE | 2622951 | A1 | 11/1977 |
| EP | 0659792 | A2 | 6/1995 |
| EP | 0689556 | A1 | 1/1996 |
| EP | 0937110 | A1 | 8/1999 |
| EP | 0978523 | A1 | 2/2000 |
| EP | 2046861 | A1 | 4/2009 |
| JP | 2013095759 | A | 5/2013 |
| JP | 2013234304 | A * | 11/2013 |
| WO | WO-9421702 | A1 | 9/1994 |
| WO | WO-9821255 | A1 | 5/1998 |
| WO | WO-2008/013731 | A1 | 1/2008 |
| WO | WO-2011/069966 | A1 | 6/2011 |
| WO | WO-2011/124710 | A1 | 10/2011 |

OTHER PUBLICATIONS

Matsumoto Abstract; JP2013234304A (Year: 2013).*
International Search Report for PCT/EP2015/051445 dated Mar. 6, 2015.

* cited by examiner

*Primary Examiner* — Jafar F Parsa
*Assistant Examiner* — Kofi Adzamli
(74) *Attorney, Agent, or Firm* — Drinker Biddle & Reath LLP

(57) ABSTRACT

The invention relates to novel silane-modified formamides and/or pre-polymers for bonding and/or sealing diverse substrate materials, such as, for example metal, wood, glass and/or plastic. The invention also relates to a reactive single-component adhesive system comprising the claimed silane-modified formamide and/or pre-polymers.

16 Claims, No Drawings

SILANE MODIFIED FORMAMIDES

CROSS-REFERENCE TO RELATED APPLICATIONS

This application is a national stage application (under 35 U.S.C. § 371) of PCT/EP2015/051445, filed Jan. 26, 2015, which claims benefit of European Application No. 14153502.1, filed Jan. 31, 2014, both of which are incorporated herein by reference in their entirety.

TECHNICAL FIELD OF THE INVENTION

The present invention relates to novel silane-modified formamides of formula (I) for the coating, adhesive bonding and/or sealing of various substrate materials, such as, for example, metal, wood, glass and/or plastics material. There is additionally provided a reactive one-component adhesive system comprising the silane-modified formamides of formula (I) according to the invention.

The silane-modified formamides of formula (I) according to the invention can further be used as starting material for the preparation of silane-modified prepolymers and polymers of formula (IV), which are likewise suitable, for example, for the coating, adhesive bonding and/or sealing of various substrate materials.

BACKGROUND OF INVENTION

Silane-modified polymers have generally been known for many years, and sealing materials or adhesives based on silane-modified prepolymers or polymers have proved to be successful for a very wide variety of applications, for example in seam sealing in automotive construction, in windows or in the structural facings sector.

Very generally, silane-modified polymers (which are in the form of prepolymers prior to processing) are understood as being polymers which comprise silane groups having hydrolysable radicals and the polymer backbone of which is not composed substantially of O—Si—O—Si chains, as is the case with silicones, but of C—C chains, which in most cases are interrupted by heteroatoms and comprise urethane, ether, ester, urea, amide and other structural units. Under the action of moisture, the radicals on the silane groups, for example usually acetate or alkoxy groups, are hydrolysed with the formation of reactive silanols, which subsequently condense and cure, with water, alcohol or acetic acid cleavage, to form a high molecular weight network.

The value of these silane-modified polymers is substantially their particular property profile. On the one hand, coating materials, adhesives or sealing materials that comprise silane-modified polymers are distinguished by strong adhesion to a very wide variety of substrates without complex pretreatment (no primer is necessary). This is because OH groups are normally present on inorganic substrate surfaces and are able to react with the reactive silanols of the polymer, which form under the action of moisture. On the other hand, the properties of the silane-modified polymers can be adapted to a large number of very different applications with the aid of the polymer backbone.

The silane-modified polyurethanes and polyureas that are currently available commercially on the market are thus based on a high molecular weight backbone which is produced (i) by reaction of NCO-containing prepolymers with aminosilanes (ii) by reaction of OH-terminated prepolymers, such as, for example, polyethers, polyurethanes or polyesters, with NCO-functional silanes, as is shown in the following formula scheme:

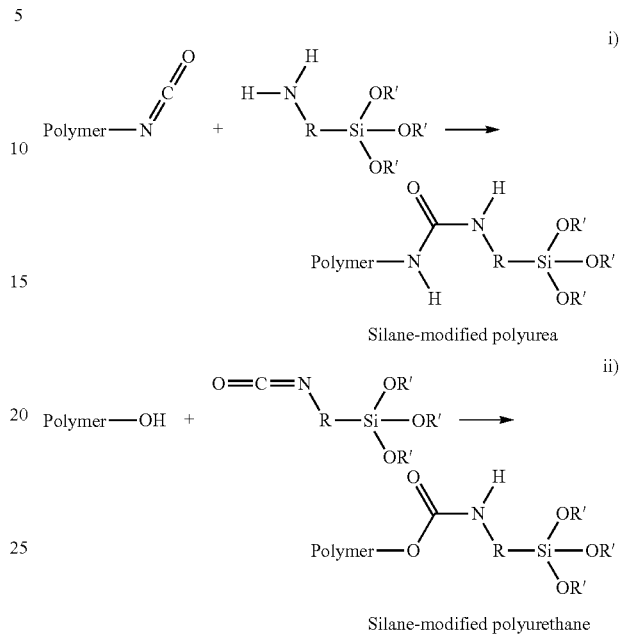

A disadvantage of coating materials, adhesives and sealing materials that are based on silane-modified polyureas is, however, the high viscosity of their prepolymers. On account of the high viscosity, the use of silane-modified polyureas is possible to only a limited extent, because the coating or sealing materials to be used must normally be applied in the liquid to pasty state to the substrate parts that are to be coated or adhesively bonded. A prepolymer that is too viscous is consequently difficult or impossible to use as a coating material, adhesive and/or sealing material.

Furthermore, the degree of hardness of the resulting coating, adhesive bond and/or seal as the end product after the silane crosslinking is critical for the particular use in question. In the case of silane-modified polyureas, end products having a high degree of hardness are normally obtained. Silane-modified polyurethanes, on the other hand, provide softer end products after curing. However, the synthesis of silane-modified polyurethanes having a high silane content is difficult to carry out economically because of the relatively expensive NCO-functionalised silane precursors.

The monomeric NCO content in silane-modified polymers additionally plays an important role in this connection: on account of the not negligible vapour pressure of the isocyanates (even at room temperature), isocyanate vapours that can be harmful to health or at least sensitising can form even during spray application. Consequently, the development of reactive prepolymers which are substantially free of isocyanate monomers and in any case are below the exposure limit value (Total Reactive Isocyanate Group concentration TRIG) according to the Technical Rules for Hazardous Substances (TRGS) 430 (edition March 2009) of 0.018 mg/m$^3$ NCO, preferably below 0.01 mg/m$^3$, particularly preferably below 0.001 mg/m$^3$, is desirable.

OBJECT OF THE PRESENT INVENTION

The object underlying the present invention is accordingly to provide an improved reactive one component adhesive and/or coating system of inexpensive and readily accessible starting materials, which system is as harmless to health as possible and largely avoids the above-described problems of known silane-modified polymers.

There is provided in particular a reactive one-component adhesive system which is simpler to handle on account of a lower viscosity and lower crystallinity and which at the same time permits high chemical stability of the end products. Also desired are polymeric end products which can be prepared inexpensively and which have an advantageous balance of properties, such as in particular degree of curing and chemical stability.

SUMMARY OF THE INVENTION

The present invention relates to compounds of formula (I) according to patent claim 1, which are suitable as a one-component adhesive system/coating system for the improved coating, adhesive bonding and/or sealing of various substrate materials, such as, for example, metal, wood, glass and/or plastics material.

The compounds of formula (I) can further be used according to the invention to provide silane-modified prepolymers of formula (IV), which can likewise be used as a one-component adhesive system/coating system for the improved coating, adhesive bonding and/or sealing of various substrate materials, such as, for example, metal, wood, glass and/or plastics material.

In the final cured state, the invention provides polymers condensed via —Si—O—Si— bridges as permanent coatings, adhesives and/or sealing materials.

The present invention further provides processes for the preparation of the compounds of formula (I) and of the prepolymers of formula (IV).

DETAILED DESCRIPTION OF THE INVENTION

According to the invention there are provided compounds of formula (I):

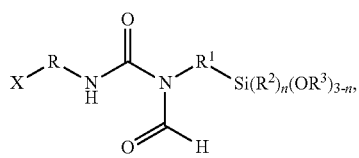

(I)

wherein in formula (I):
X represents an optionally substituted, linear or branched, aliphatic, alicyclic, araliphatic, heterocyclic and/or aromatic structural unit having from 1 to 40 carbon atoms, wherein one or more non-adjacent methylene groups can each be replaced by O or S; or X represents —H or —NCO;
R represents an at least divalent, optionally substituted, linear or branched, aliphatic, alicyclic, araliphatic and/or aromatic structural unit having from 1 to 40 carbon atoms, wherein one or more non-adjacent methylene groups can each be replaced by O or S;
$R^1$ represents an at least divalent, optionally substituted, linear or branched, aliphatic, alicyclic, araliphatic and/or aromatic structural unit having from 1 to 12 carbon atoms, wherein one or more non-adjacent methylene groups can each be replaced by O or S;

$R^2$ and $R^3$ each independently of the other represents an optionally substituted, linear or branched, aliphatic group having from 1 to 12 carbon atoms; and n represents an integer from 0 to 2.

In one embodiment according to the invention, compounds of formula) are consequently provided.

In a further embodiment according to the invention, a silane-modified prepolymer of formula (IV) is provided:

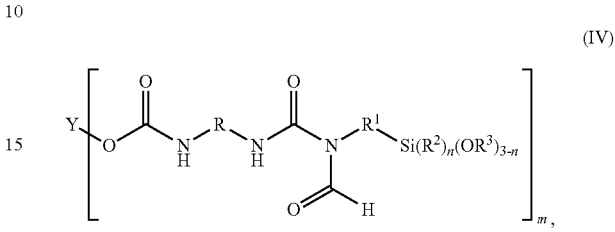

(IV)

wherein R, $R^1$, $R^2$, $R^3$ and n have the meanings given above, Y is an m-valent, optionally substituted, linear or branched, aliphatic, alicyclic, araliphatic, heterocyclic and/or aromatic structural unit having from 1 to 40 carbon atoms or represents a structural unit reduced by m OH radicals of a polyhydric alcohol (polyol) or of a polyurethane, polyurea, polyester, polyether, polycarbonate, polyacetal, polyacrylate, polyester amide or polythioether polyol and m is a number from 1 to 10, wherein in this case m can also be a fraction, for example when Y is a polyacrylate having a mean OH group content of 2.4.

In a further embodiment according to the invention there is provided a process for the preparation of the compound of formula (I), comprising reacting the silane-modified formamide of formula (Ia) with the isocyanate of formula (Ib):

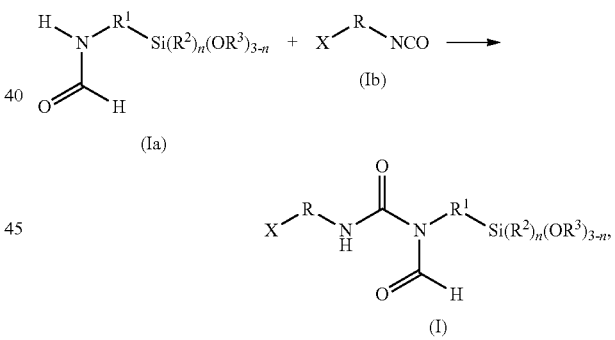

wherein the groups X, R, $R^1$, $R^2$, $R^3$ and n are as defined in claim 1.

In a further embodiment according to the invention there is disclosed a process (A) for the preparation of the silane-modified prepolymer of formula (IV):

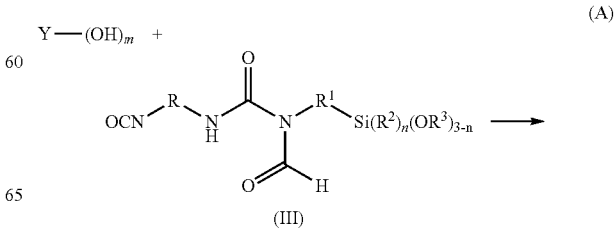

(A)

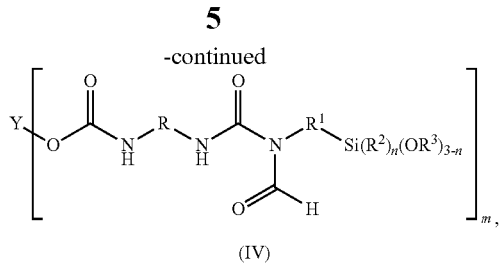

(IV)

wherein the variables are as defined fear formula (I).

In a further embodiment according to the invention there is provided a reactive one-component adhesive system or coating system comprising at least one compound of formula (I) and/or at least one compound of formula (IV).

According to the invention, the compound of formula (I) and/or the compound of formula (IV) is used for the production of adhesives and sealing materials, lacquers, coatings, sizes, inks and/or printing inks.

In a further embodiment according to the invention there is described the use of the reactive one-component adhesive system or coating system according to the invention for the coating, adhesive bonding and/or sealing of metal, wood, wood-based materials, glass, leather, textiles, plastics materials, mineral materials, cork, fibres, concrete, paper, cardboard and films.

There is additionally disclosed according to the invention a composite that is bonded by the one-component adhesive system according to the invention.

Definitions

As used herein, the term "alicyclic" is to denote carbocyclic or heterocyclic compounds which do not belong to the aromatic compounds, such as, for example, cycloalkanes cycloalkenes or oxa-, thia-, aza- or thiaza-cycloalkanes. Specific examples thereof are cyclohexyl groups, cyclopentyl groups and also derivatives thereof interrupted by one or two N or O atoms, such as, for example, pyrimidine, pyrazine, tetrahydropyran or tetrahydrofuran.

As used herein, the term "araliphatic" is to denote alkyl radicals substituted by aryl groups, such as, for example, benzyl, phenylethyl, biphenyl, etc.

As used in this application, the expression "optionally substituted" or "substituted" is to denote in particular the substitution of the relevant structural unit by —F, —Cl, —I, —Br, —OH, —OCH$_3$, —OCH$_2$CH$_3$, —O-n-propyl or —O-isopropyl, —OCF$_3$, —CF$_3$, —CF$_3$, —S—C$_{1-6}$-alkyl and/or another linear or branched, aliphatic, alicyclic, araliphatic and/or aromatic structural unit having from 1 to 12 carbon atoms that is optionally linked via a heteroatom. Preferably, it denotes substitution by halogen (in particular —F, —Cl), C$_{1-6}$-alkoxy (in particular methoxy and ethoxy), hydroxy, trifluoromethyl and trifluoromethoxy.

As used in this application, the expression "low molecular weight" is to denote compounds whose molecular mass does not exceed approximately 800 g·mol$^{-1}$.

As used in this application, the expression "high molecular weight" is to denote compounds whose molecular mass exceeds approximately 800 g·mol$^{-1}$.

In the case of compounds whose molecular mass does not follow from an exactly defined structural formula, such as, for example, in the case of polymers, the molecular mass is to be understood as being the weight-average molecular weight in each case.

As used in this application, the term "monomer" is to denote a low molecular weight compound with functional groups which is involved in the synthesis of oligomers and/or (pre)polymers and has a defined molar mass.

As used in this application, the term "oligomer" is to denote a compound in which only a few monomers of the same type or of different types are linked repeatedly to one another.

As used in this application, the term "prepolymer" is to denote oligomeric compounds with functional groups which are involved in the final synthesis of polymers.

As used in this application, the term "polymer" is to denote high molecular weight compounds in which monomers, oligomers and/or prepolymers of the same type or of different types are linked repeatedly to one another and which can differ in terms of degree of polymerisation, molar mass distribution or chain length.

EMBODIMENTS ACCORDING TO THE INVENTION

Embodiments according to the invention are described in detail hereinbelow.

Compounds of Formulae (I), (II) and (III)

In one embodiment there are provided the compounds of the general formula (I):

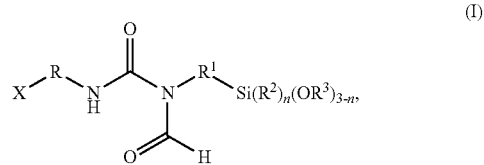

(I)

wherein in formula (I):
X represents hydrogen, —NCO or an optionally substituted, linear or branched, aliphatic, alicyclic, araliphatic, heterocyclic and/or aromatic structural unit having from 1 to 40 carbon atoms, wherein one or more non-adjacent methylene groups can each be replaced by O or S;
R represents an at least divalent, optionally substituted, linear or branched, aliphatic, alicyclic, araliphatic and/or aromatic structural unit having from 1 to 40 carbon atoms, wherein one or more non-adjacent methylene groups can each be replaced by O or S;
R$^1$ represents an at least divalent, optionally substituted, linear or branched, aliphatic, alicyclic, araliphatic and/or aromatic structural unit having from 1 to 12 carbon atoms, wherein one or more non-adjacent methylene groups can each be replaced by O or S;
R$^2$ and R$^3$ each independently of the other represents an optionally substituted, linear or branched, aliphatic group having from 1 to 12 carbon atoms; and
n represents an integer from 0 to 2.

In a preferred embodiment there are provided the compounds of formula (II):

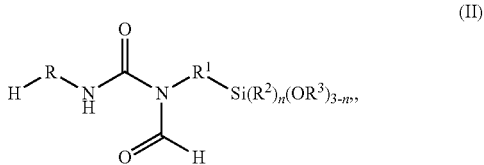

(II)

wherein R, $R^1$, $R^2$, $R^3$ and n are as defined for formula (I).

In a particularly preferred embodiment there are provided the compounds of formula (III):

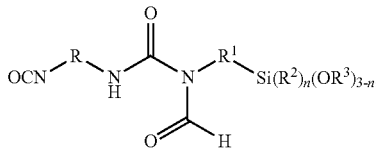

wherein R, $R^1$, $R^2$, $R^3$ and a are as defined for formula (I).

Preferred Substituent Meanings in Formulae (I), (II) and (III)

There are preferably provided compounds of formula (I), (II) and/or (III) wherein in each case:

R represents methylene ($-CH_2-$), ethylene ($-CH_2CH_2-$), propylene ($-CH_2CH_2CH_2-$), isophorylene, 4,4'-dicyclohexylmethylene, bis(cyclohexylene), 4,4'-bisphenylene, o-, m- or p-tolylene, or hexylene (in particular $-CH_2CH_2CH_2CH_2CH_2CH_2-$), and particularly preferably n-hexylene;

$R^1$ represents methylene ($-CH_2-$) or propylene (in particular n-propylene $-CH_2CH_2CH_2-$), particularly preferably n-propylene;

$R^2$ and $R^3$ each independently of the other represents methyl or ethyl, preferably ethyl; and n represents an integer from 0 to 2.

There are particularly preferably provided compounds of formula (I), (II) and/or (III) wherein in each case:

R represents isophorylene, 4,4'-dicyclohexylmethylene, bis(cyclohexylene), bisphenylene, tolylene or n-hexylene;

$R^1$ represents n-propylene;

$R^2$ and $R^3$ each independently of the other represents methyl or ethyl; and n represents an integer from 0 to 2.

There are most particularly preferably provided compounds of formula (III) wherein R is isophorylene, tolylene or n-hexylene, $R^1$ is n-propylene, $R^2$ and $R^3$ are methyl and n=0.

The compounds of formulae (I), (II) and (III) according to the invention are themselves suitable as low molecular weight hinders for coatings or adhesives and/or sealing materials. Alternatively, the compounds of formula (III) according to the invention can be used for the preparation of higher molecular weight prepolymers or polymers, which in turn are suitable as binders for coatings or adhesives and/or sealing materials.

The compounds of formula (I) according to the invention have viscosities (at 23° C., measured by means of a Physica MCR 51 rheometer from Anton Paar Germany GmbH (DE) in accordance with DIN EN ISO 3219) in the range of from 100 to 10,000 mPa·s, preferably from 100 to 7000 mPa·s, particularly preferably from 100 to 5000 mPa·s.

The compounds of formula (I) according to the invention are to be classified in respect of their viscosity between silane-modified polyureas and silane-modified polyurethanes, so that an inexpensive optimisation of the viscosity as compared with silane-modified polyureas is possible by means of the compounds according to the invention.

Process for the Preparation of the Compounds According to the Invention

The compounds of formula (I) according to the invention can be prepared by the following two-stage process, wherein the groups X, R, $R^1$, $R^2$, $R^3$ and a are as defined for formula (I) and R' preferably represents an alkyl group having from 1 to 4 carbon atoms:

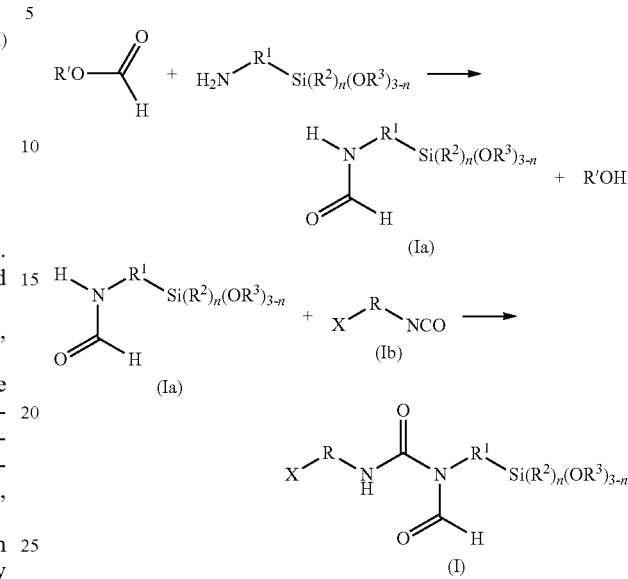

An excess of the formic acid alkyl ester R'O—CHO is preferably first added dropwise to the amine $H_2N-R^1-Si(R^2)_n(OR^3)_{3-n}$, R' preferably representing an alkyl group having from 1 to 4 carbon atoms. Methyl formate or ethyl formate is particularly preferred as the formic acid alkyl ester R'O—CHO. Preferably, 1 mol of amine is reacted with an excess of from 1.01 to 6 mol of formic acid alkyl ester R'O—CHO, particularly preferably from 1.05 to 4 mol, at the boiling temperature of the formic acid alkyl ester. When the reaction is complete, excess formic acid alkyl ester R'O—CHO and the resulting alcohol R'—OH are distilled off by means of film distillation and the resulting product (Ia) is optionally filtered off.

The compound of formula (Ia) is then reacted with X—R—NCO, preferably under inert conditions, at temperatures of from 20 to 200° C., preferably from 40 to 160° C. Depending on the substituent X in X—R—NCO, the two components are used in an equivalent ratio of isocyanate groups to formamide groups of from at least 1:1 to not more than 40:1, preferably from 8:1 to not more than 30:1 and particularly preferably from 10:1 to not more than 25:1. The reaction can be carried out in solution or solvent-free, but preferably solvent-free. In order to separate off excess X—R—NCO, the reaction mixture is subsequently passed at a suitable feed rate, such as, for example, 600 ml/h, over a thin-film evaporator under reduced pressure, for example at a pressure of less than 1.0 mbar, preferably less than 0.5 mbar, particularly preferably less than 0.2 mbar, under conditions that are as gentle as possible, for example at a temperature of from 100 to 200° C., preferably from 120 to 180° C.

The preparation of the compounds having the formula (I) can be carried out without the use of catalysts. However, known catalysts can optionally also be added in order to accelerate the reaction. There can be used, for example, tertiary amines, such as, for example, triethylamine, tributylamine, dimethylbenzylamine, diethylbenzylamine, pyridine, methylpyridine, dicyclohexylmethylamine, dimethylcyclohexylamine, N,N,N',N-tetramethyldiaminodiethyl ether, bis-(dimethylaminopropyl)-urea, N-methyl- or N-ethyl-morpholine, N-cocomorpholine, N-cyclohexylmorpholine, N,N,N',N'-tetramethylethylenediamine, N,N,N',N'-tetramethyl-1,3-butanediamine, N,N,N,N'-tetramethyl-1,6-hexanediamine, pentamethyldiethylenetriamine, N-methylpiperidine, N-dimethyl-aminoethylpiperidine, N,N'-dimethylpiperazine, N-methyl-N''-dimethylaminopiperazine, 1,2-dimethylimidazole, 2-methylimidazole, N,N-dimethylimidazole-B-phenylethylamine, 1,4-diazabicyclo-(2,2,2)-octane (DABCO) and bis-(N,N-dimethylaminoethyl) adipatc, amidines, such as, for example, 1,5-diazabicyclo[4.3.0]nonene (DBN), 1,8-diazabicyclo(5.4.0)undec-7-ene (DBU) and 2,3-dimethyl-3,4,5,6-tetrahydropyrimidine, alkanolamine compounds, such as, for example, triethanolamine, triisopropanolamine, N-methyldiethanolamine, N-ethyl-diethanolamine, dimethylaminoethanol and 2-(N,N-dimethylaminoethoxy)ethanol, N,N',N''-tris-(dialkylaminoalkyl)hexahydrotriazines, such as, for example, N,N',N''-tris-(dimethylaminopropyl)-s-hexahydrotriazine, bis(dimethylaminoethyl) ether and also metal salts, such as, for example, inorganic and/or organic compounds of iron, lead, bismuth, zinc and/or tin in conventional oxidation states of the metal, for example iron(II) chloride, iron(III) chloride, bismuth(III) 2-ethylhexanoate, bismuth (III) octoate, bismuth(III) neodecanoate, zinc chloride, zinc 2-ethylcaproate, zinc(II) trifluoromethanesulfonate (zinc triflate), tin(II) octoate, tin(II) ethylcaproate, palmitate, dibutyltin(IV) dilaurate (DBTL), dibutyltin(IV) dichloride or lead octoate.

Preferred catalysts that are to be used are tertiary amines, amidines and tin compounds or zinc compounds of the mentioned type. Particularly preferred catalysts are 1,4-diazabicyclo-(2,2,2)-octane (DABCO), 1,5-diazabicyclo [4.3.0]nonene (DBN), 1,8-diazabicyclo(5.4.0)undec-7-ene (DBU) as well as dibutyltin(IV) dilaurate (DBTL) and zinc(II) trifluoromethanesulfonate (zinc triflate).

The catalysts mentioned by way of example above can be used in the reaction individually or in the form of arbitrary mixtures and are employed, if at all, in amounts of from 0.001 to 1.0 wt. %, preferably from 0.01 to 0.5 wt. %, calculated as the total amount of catalysts used, based on the total amount of starting compounds used.

The progress of the reaction can be monitored, for example, by determining the NCO content by titrimetry. When the desired NCO content has been reached, the reaction is terminated.

Particularly preferably, the compounds of formula (III) according to the invention are prepared by the above-mentioned process, wherein the groups R, $R^1$, $R^2$, $R^3$ and n are as defined for formula (I):

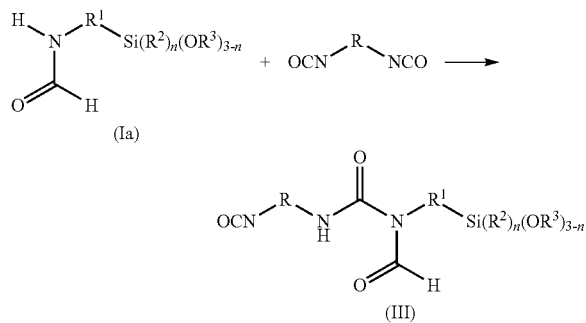

A silane-modified formamide having the formula (Ia) is hereby reacted with a diisocyanate OCN—R—NCO, preferably under an inert protecting gas atmosphere e.g. nitrogen or argon).

Suitable diisocyanates OCN—R—NCO for the preparation of silane-modified formamides of formula (III) are selected, for example, from the group consisting of 1,4-, 1,3- and/or 1,2-cyclohexane diisocyanate, 1-methyl-2,4-diisocyanato-cyclohexane, 1-methyl-2,6-diisocyanato-cyclohexane, tetramethylene diisocyanate, octamethylene diisocyanate, decamethylene diisocyanate, dodecamethylene diisocyanate, $H_6$-2,4- and/or -2,6-diisocyanatotoluene, 4,4'-diisocyanatodiphenylmethane, 2,4'-diisocyanatodiphenylmethane, 2,2'-diisocyanatodiphenylmethane, meta- and/or para-xylylene diisocyanate, 2,4-diisocyanatotoluene and/or 2,6-diisocyanatotoluene, isopropenyldintethyltoluylene diisocyanate, α, α, α', α,'-tetra-methyl-m- and/or -p-xylylene diisocyanate, 1,6-hexamethylene diisocyanate, trimethylhexane diisocyanate, tetramethylhexane diisocyanate, nonane triisocyanate, 1-isocyanato-3,3,5-trimethyl-5-isocyanatomethylcyclohexane (isophorone diisocyanate), 4,4'-diisocyanatodicyclohexylmethane and/or 2,4'-diisocyanatodicyclohexylmethane and/or 2,2'-diisocyanatodicyclohexylmethane and mono- and di-methyl-substituted derivatives thereof.

There are particularly preferably used for OCN—R—NCO hexamethylene diisocyanate (HDI), isophorone diisocyanate (IPDI), 2,4-diisocyanatotoluene (TIM) and/or 2,6-diisocyanatotoluene, 4,4'-diisocyanatodiphenylmethane, 2,4'-diisocyanatodiphenylmethane, 2,2'-diisocyanatodiphenylmethane or isomer mixtures thereof.

The reaction of the compounds of formula (Ia) with OCN—R—NCO takes place at temperatures of from 20 to 200° C., preferably from 40 to 160° C. The two components are thereby used in an equivalent ratio of isocyanate groups to formamide groups of from at least 6:1 to not more than 40:1, preferably from 8:1 to not more than 30:1 and particularly preferably from 10:1 to not more than 25:1. The reaction can be carried out in solution or solvent-free, but preferably solvent-free.

The preparation of the compounds having the formula (III) can be carried out without use of catalysts. However, the catalysts mentioned above for the preparation of the compounds of formula (I) can optionally also be used concomitantly in order to accelerate the reaction.

Particularly preferred catalysts are 1,4-diazabicyclo-(2,2,2)-octane (DABCO), 1,5-diazabicyclo[4.3.0]nonene (DBN), 1,8-diazabicyclo(5.4.0)undec-7-ene (DBU) as well as dibutyltin(IV) dilaurate (DBTL) and zinc(II) trifluoromethanesulfonate (zinc triflate).

The catalysts mentioned by way of example above can be used in the reaction individually or in the form of arbitrary mixtures and are employed, if at all, in amounts of from 0.001 to 1.0 wt. %, preferably from 0.01 to 0.5 wt. %, calculated as the total amount of catalysts used, based on the total amount of starting compounds used.

The progress of the reaction can again be monitored, for example, by determining the NCO content by titrimetry. When the desired NCO content has been reached, the reaction is terminated.

In a preferred embodiment, after the reaction of the compounds of formula (Ia) with the diisocyanate OCN—R—NCO, an unreacted excess of monomeric diisocyanate OCN—R—NCO is separated from the reaction product to a residual content of less than 1 wt. %, preferably of less than 0.5 wt. %, particularly preferably of less than 0.3 wt. %, based on the total mass of the reaction product. The reaction mixture is preferably freed of excess monomeric diisocyanates OCN—R—NCO by film distillation in vacuo, for example at a pressure of less than 1.0 mbar, preferably less than 0.5 mbar, particularly preferably less than 0.2 mbar, under conditions that are as gentle as possible, for example at a temperature of from 100 to 200° C., preferably from 120 to 180° C.

The reaction mixtures worked up in that manner generally yield product mixtures which comprise more than 85 wt. %, preferably more than 95 wt. %, of compounds of formula (III) according to the invention, less than 1 wt. % of monomeric (unreacted) diisocyanate and less than 15 wt. %, preferably less than 10 wt. %, of compounds of formula (IIIa) hereinbelow, based on the total mass of the reaction product.

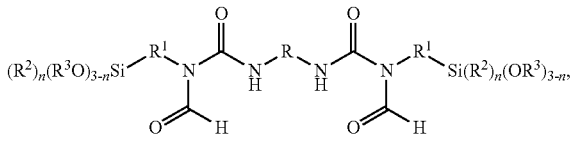
(IIIa)

wherein the variables are as defined for formula (I).

The compounds of formula (III) prepared in that manner are clear, virtually colourless products which, depending on the chosen starting diisocyanate, are low- to high-viscosity liquids and have residual contents of monomeric starting diisocyanates of less than 1.0 wt. %, preferably of less than 0.5 wt. %, particularly preferably of less than 0.3 wt. %, based on the total mass of the reaction product.

In order to prevent premature crosslinking of the silane groups of the compounds of formula (I) and/or (III) during the preparation according to the invention, it can be advantageous to add water acceptors. For example, there can be used orthoformic esters, such as, for example, triethyl orthoformate, vinylsilanes, such as, for example, vinyltrimethoxysilane, or organic phosphates, such as, for example, dibutyl phosphate. The water acceptors are used, if necessary, in amounts of up to 5 wt. %, preferably up to 2 wt. %, based on the total amount of starting materials.

If catalysts and/or water acceptors are used, they can be added to the starting compounds before the start of the actual reaction. It is, however, also possible to add these auxiliary substances to the reaction mixture at any desired point in time during the reaction.

In a preferred embodiment, the processes described herein take place under a protecting gas atmosphere, such as, for example, nitrogen.

Silane-Modified Compounds of Formula (IV)

Particularly preferably, the compounds of formula (III) as defined above are used for the preparation of silane-modified compounds or prepolymers having the formula (IV):

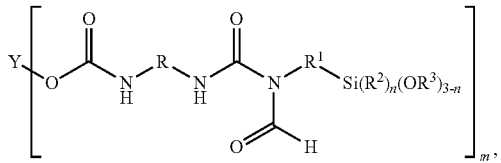
(IV)

wherein R, R¹, R², R³ and n have the meanings given in claim 1, Y is an m-valent, optionally substituted, linear or branched, aliphatic, alicyclic, araliphatic, heterocyclic and/or aromatic structural unit having from 1 to 40 carbon atoms or a structural unit reduced by m OH radicals of a polyol or of a polyurethane, polyurea, polyester, polyether, polycarbonate, polyacetal, polyacrylate, polyester amide or polythioether polyol, and m is a number (optionally also a rational number) from 1 to 10.

There are particularly preferably provided compounds of formula (IV) wherein it is n-hexylene, R¹ is n-propylene, R² and R³ are methyl and n=0.

Process for the Preparation of the Silane-Modified Compounds of Formula (IV)

The silane-modified prepolymers of formula (IV) according to the invention can be prepared by process (A) described hereinbelow:

(A)

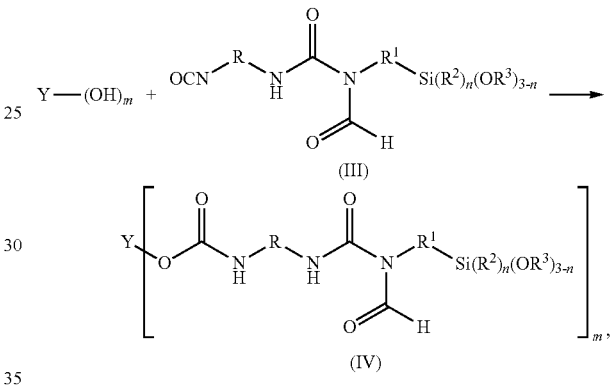

wherein R, R¹, R², R³, n, Y and m are as defined in claim 7.

According to the invention, the compound of formula (IV) can be prepared by reacting Y—(OH)$_m$ with a compound of formula (III) prepared as described above.

There can be used for Y—(OH)$_m$, for example, polyhydric alcohols and/or ether or ester alcohols having from 2 to 14 carbon atoms, preferably from 4 to 10 carbon atoms, such as, for example, 1,2-ethanediol, 1,2- and 1,3-propanediol, the isomeric butanediols, pentanediols, hexanediols, heptanediols and octanediols, 1,10-decanediol, 1,12-dodecanediol, 1,2- and 1,4-cyclohexanediol, 1,4-cyclohexanedimethanol, 1,4-bis(2-hydroxyethoxy)-benzene, 2,2-bis-(4-hydroxyphenyl)-propane (bisphenol A), 2,2-bis-(4-hydroxycyclohexyl)-propane (perhydro-bisphenol), 1,2,3-propanetriol, 1,2,4-butanetriol, 1,1,1-trimethylolethane, 1,2,6-hexanetriol, 1,1,1-trimethylolpropane (TMP), bis-(2-hydroxyethyl)-hydroquinone, 1,2,4- and 1,3,5-trihydroxy-cyclohexane, 1,3,5-tris(2-hydroxyethyl) isocyanurate, 3(4),8(9)-bis-(hydroxymethyl)-tricyclo[5.2.1.0$^{2,6}$]decane, di-trimethylolpropane, 2,2-bis(hydroxymethyl)-1,3-propanediol (pentaerythritol), 2,2,6,6-tetrakis(hydroxymethyl)-4-oxa-heptane-1,7-diol (dipentaerythritol), mannitol or sorbitol, low molecular weight ether alcohols, such as, for example, diethylene glycol, triethylene tetraethylene glycol, dipropylene glycol or dibutylene glycol, or low molecular weight ester alcohols, such as, for example, hydroxypivalic acid neopentyl glycol ester, and/or mixtures of the compounds mentioned above.

The radical Y is preferably a radical which is derived from a polymeric polyol, polyether polyol, polyester polyol, polycarbonate polyol and/or polyacrylate polyol, as are known in polyurethane chemistry. These polymeric polyols usually have a number-average molecular weight of from 200 to 22,000, preferably from 250 to 18,000, particularly preferably from 250 to 12,000. A broad overview of suitable polymeric polyols will be found, for example, in N. Adam et al.: "Polyurethanes", Ullmann's Encyclopedia of Industrial Chemistry, Electronic Release, 7th ed., chap. 3.2-3.4, Wiley-Val, Weinheim 2005.

Suitable polyether polyols are, for example, those of the type mentioned in DE 26 22 951 B, column 6, line 65 to column 7, line 26, in EP-A 0 978 523, page 4, line 45 to page 5, line 14 or in WO 2011/069966, page 4, line 20 to page 5, line 23, provided they comply with the requirements given above in respect of functionality and molecular weight. Particularly preferred polyether polyols are addition products of ethylene oxide and/or propylene oxide on 1,2-propanediol, 1,3-propanediol, glycerol, trimethylolpropane, ethylenediamine and/or pentaerythritol, or the polytetramethylene ether glycols having number-average molecular weights of from 400 g/mol to 4000 g/mol obtainable, for example, according to Angew. Chem, 7, 927 (1960) by polymerisation of tetrahydrofuran.

Suitable polyester polyols are, for example, those of the type mentioned in EP-A 0 978 523, page 5, lines 17 to 47 or in EP-A 0 659 792, page 6, lines 32 to 45, provided they comply with the requirements given above in respect of functionality and molecular weight. Particularly preferred polyester polyols are condensation products of polyhydric alcohols, such as, for example, 1,2-ethanediol, 1,2-propanediol, diethylene glycol, 1,4-butanediol, 1,6-hexanediol, neopentyl glycol, 1,4-cyclohexanedimethanol, 1,4-cyclohexanediol, perhydrobisphenol, 1,1,1-trimethylolpropane, 1,2,3-propanetriol, pentaerythritol and/or sorbitol, with deficient amounts of polyvalent carboxylic acids or carboxylic anhydrides, such as, for example, succinic acid, adipic acid, sebacic acid, dodecanedioic acid, glutaric anhydride, maleic anhydride, phthalic anhydride, isophthalic acid, terephthalic acid, trimellitic acid, hexahydrophthalic anhydride and/or tetrahydrophthalic anhydride, or those which are obtainable in a manner known per se from lactones, such as, for example, ε-caprolactone, and simple monohydric alcohols, such as, for example, those mentioned above, as starter molecules with ring opening.

Suitable polycarbonate polyols are in particular the reaction products known per se of dihydric alcohols, for example those mentioned by way of example above in the list of polyhydric alcohols, with diaryl carbonates, such as, for example, diphenyl carbonate, dimethyl carbonate or phosgene. Suitable poly-carbonate polyols are also those which, as well as comprising carbonate structures, additionally comprise ester groups. They are in particular the polyester carbonate diols known per se, as can be obtained, for example, according to the teaching of DE-AS 1 770 245 by reaction of dihydric alcohols with lactones, such as in particular ε-caprolactone, and subsequent reaction of the resulting polyester diols with diphenyl carbonate or dimethyl carbonate. Suitable polycarbonate polyols are also those which, as well as comprising carbonate structures, additionally comprise ether groups. They are in particular the polyether carbonate polyols known per se, as are obtainable, for example, by the process of EP-A 2046861 by catalytic reaction of alkylene oxides (epoxides) and carbon dioxide in the presence of H-functional starter substances.

Suitable polyacrylate polyols are, for example, those of the type mentioned in WO 2011/124710, page 10, line 32 to page 13, line 18, provided they comply with the requirements given above in respect of functionality and molecular weight. Particularly preferred polyacrylate polyols are polymers or copolymers of hydroxyalkyl esters of acrylic acid or methacrylic acid, such as, for example, hydroxyethyl (meth)acrylate, hydroxypropyl (meth)acrylate or hydroxybutyl (meth)acrylate, optionally together with acrylic acid alkyl esters and/or methacrylic acid alkyl esters, such as, for example, methyl (meth)acrylate, ethyl (meth)acrylate, n-butyl (meth)acrylate, isobutyl (meth)acrylate, 2-ethylhexyl (meth)acrylate, cyclohexyl (meth)acrylate, isobornyl (meth)acrylate, lauryl (meth)acrylate, styrene or other copolymerisable olefinically unsaturated monomers, such as, for example, acrylic acid, methacrylic acid or maleic acid dimethyl ester.

Suitable polyols are, for example, also the known polyacetal polyols obtainable by reaction of simple glycols, such as, for example, diethylene glycol, triethylene glycol, 4,4'-dioxethoxy-diphenyl-dimethylmethane (adduct of 2 mol of ethylene oxide on bisphenol A) or hexanediol, with formaldehyde, or also polyacetals prepared by polycondensation of cyclic acetals, such as, for example, trioxane.

Further suitable polyols are, for example, also the specific polyols described in EP-A 0 689 556 and EP-A 0 937 110, for example obtainable by reaction of epoxidised fatty acid esters with aliphatic or aromatic polyols with epoxide ring opening.

Hydroxyl-group-containing polybutadienes can likewise be used as polyols. In a preferred embodiment of the invention, polyether, polyester, polycarbonate anchor polyacrylate polyols are used as component Y—(OH)$_m$.

The polyols are used in the process according to the invention individually or in the form of arbitrary mixtures with one another. They can be present both in solvent-free form and in solution in conventional solvents.

The reaction of the compounds of the formula Y—(OH)$_m$ with compounds of formula (III) takes place at temperatures of from 20 to 200° C., preferably from 40 to 160° C. An equivalent ratio of isocyanate groups to hydroxyl groups of from 0.7:1 to 1.2:1, preferably from 0.8:1 to 1.1:1, particularly preferably from 0.9:1 to 1.05:1, is maintained.

The process according to the invention can be carried out without catalysis. However, in order to accelerate the urethanisation reaction, catalysts conventional in isocyanate chemistry can optionally also be used concomitantly. Suitable catalysts have already been described above for the preparation of the compound of formula (I).

Particularly preferred catalysts are 1,4-diazabicyclo-(2,2,2)-octane (DABCO), 1,5-diazabicyclo[4.3.0]nonene (DBN), 1,8-diazabicyclo(5.4.0)undec-7-ene (DBU) and dibutyltin(IV) dilaurate (DBTL).

These catalysts can be used in the process according to the invention individually or in the form of arbitrary mixtures with one another and are employed, if necessary, in amounts of from 0.001 to 1.0 wt. %, preferably from 0.01 to 0.5 wt. %, calculated as the total amount of catalysts used, based on the total amount of starting materials.

The silane-modified compounds or prepolymers of formula (IV) according to the invention that are prepared by the process are clear, virtually colourless products which, depending on the chosen starting diisocyanate and polyol, are low- to high-viscosity liquids and contain residual contents of monomeric starting diisocyanates of less than 1.0 wt. %, preferably of less than 0.5 wt. %, particularly preferably of less than 0.3 wt. %, based on the total mass of the reaction product.

Any residual NCO contents that are still detectable can generally be taken up by addition of methanol.

In order to prevent premature crosslinking of the silane groups during the process according to the invention, it can be advantageous to add water acceptors. For example, orthoformic esters, such as, for example, triethyl orthoformate, vinylsilanes, such as, for example, vinyltrimethoxysilane, or organic phosphates, such as, for example, dibutyl phosphate, can be used. The water acceptors are used, if necessary, in amounts of up to 5 wt. %, preferably tip to 2 wt. %, based on the total amount of starting materials.

When catalysts and/or water acceptors are used concomitantly, they can be added to the starting compounds before the start of the actual reaction. It is, however, also possible to add these auxiliary substances to the reaction mixture at any desired point in time during the urethanisation reaction.

The progress of the reaction can be monitored according to the invention, for example, by titrimetric determination of the NCO content or by IR spectroscopy. Following the urethanisation reaction, that is to say when the isocyanate and hydroxyl groups or formamide groups have reacted completely, there are obtained as products of the process according to the invention the silane-modified acylurea-group-containing prepolymers of formula (IV) according to the invention.

Depending on the field of application, the compounds or prepolymers of formula (IV) according to the invention have viscosities in the range of from 10 to 1,000,000 mPa·s, preferably from 50 to 500,000 mPa·s, particularly preferably from 500 to 200,000 mPa·s.

The silane-modified prepolymers of formula (IV) disclosed herein can be used according to the invention for the production of adhesives and sealing materials, coatings, sizes, inks and/or printing inks.

The advantage of this process is that the properties of the silane-modified prepolymers of formula (IV) can be adapted to a large number of very different applications via the compounds of the formula Y—(OH)$_m$ that are used or the diisocyanates that are used.

Reactive One-Component Adhesive System

According to the invention, the compounds of formula (I) as described above and/or the compounds of formula (IV) as described above are used for a reactive one-component adhesive system. The reactive one-component adhesive system is characterised in that it comprises at least one compound of formula (I) and/or at least one compound of formula (IV).

Under the action of moisture or water, hydrolysis of the hydrolysable radicals of the silane groups takes place, followed by crosslinking (curing) of the silanols formed thereby, with cleavage of water.

Catalysts that accelerate the hydrolysis and condensation of the silanol groups can also be used concomitantly. Such catalysts are known to a person skilled in the art. There can be used, for example, acids, such as, for example, sulfuric acid, p-toluenesulfonic acid, trifluoromethanesulfonic acid, acetic acid, trifluoroacetic acid and dibutyl phosphate, bases, such as, for example, N-substituted amidines, such as 1,5-diazabicyclo[4.3.0]non-5-ene (DBN) and 1,5-diazabicyclo-[5.4.0]undec-7-ene (EMU), but also metal salts and metal chelates, such as, for example, tetraisopropyl titanate, tetrabutyl titanate, titanium(IV) acetylacetonate, aluminium tri-sec-butylate, aluminium acetylacetonate, aluminium triflate or tin triflate.

These catalysts are used, if at all, in amounts of up to 5 wt. %, preferably up to 2 wt. %, based on the weight of the silane-modified prepolymers that are used. Depending on the nature and amount of the catalyst used, curing of the one-component adhesive system formulated from the compounds of formula (I) and/or (IV) according to the invention can take place over a wide temperature range, for example from −20 to 200° C., preferably from 0 to 180° C., particularly preferably from 20 to 160° C.

There can optionally be added to the reactive one-component adhesive system according to the invention as reaction partners also any desired further hydrolysable silane compounds, such as, for example, tetramethoxysilane, tetraethoxysilane, methyltrimethoxysilane, methyltriethoxysilane, ethyltriethoxysilane, isobutyltrimethoxysilane, isobutyltriethoxysilane, octyltriethoxysilane, octyltrimethoxysilane, (3-glycidyloxypropyl)-methyldiethoxysilane, (3-glycidyloxypropyl)-trimethoxysilane, phenyltrimethoxysilane, phenyltriethoxysilane or silane-functional copolymers of the type mentioned in U.S. Pat. No. 4,499,150, or mixtures of such silane compounds.

The reactive one-component adhesive system of the invention can likewise optionally comprise further additives and/or auxiliary substances which are known in the prior art. Mention may be made of for example, pigments, antioxidants, water acceptors, fillers, slip additives, flow agents, rheology additives, foam stabilisers, hydrophobising agents, air void formers, adhesion-enhancing additives (adhesion promoters), compounding agents, plasticisers, anti-ageing agents, flame retardants and/or UV stabilisers.

There may be mentioned as suitable fillers, for example, carbon black, precipitated silicas, pyrogenic silicas, mineral chalks and precipitated chalks. Examples of suitable plasticisers which may be mentioned are phthalic acid esters, adipic acid esters, alkylsulfonic acid esters of phenol, phosphoric acid esters or also higher molecular weight polypropylene glycols.

There may be mentioned as water acceptors in particular alkoxysilyl compounds such as vinyltrimethoxysilane, methyltrimethoxysilane, isobutyltrimethoxysilane, hexadecyltrimethoxy-silane.

There are used as adhesion promoters the known functional silanes such as, for example, aminosilanes of the type mentioned above, but also N-aminoethyl-3-amino-propyl-trimethoxy- and/or N-aminoethyl-3-aminopropyl-methyl-dimethoxy-silane, epoxysilanes and/or mercaptosilanes.

As well as being used as a one-component adhesive system, the compounds of formula (I) and/or (IV) according to the invention can also be added to conventional one-component and/or two-component polyurethane adhesive systems, for example as an additive.

If the reactive one-component adhesive system according to the invention, as described above, is applied beforehand to the substrates that are to be bonded, permanent bonding or sealing of the substrates occurs as a result of the above-described crosslinking.

It may be necessary for the surfaces of the substrates that are to be bonded to be pretreated by a physical, chemical and/or physical-chemical process. The application of a primer or of an adhesion promoter composition, for example, is advantageous here but is not absolutely necessary according to the invention.

Substrates

Suitable substrates which are suitable for adhesive bonding and/or sealing by means of the reactive one-component adhesive system according to the invention are metals, glass, wood, concrete, stone, ceramics, textiles and/or plastics materials. The substrates that are to be bonded can be the same or different.

In a preferred embodiment, the reactive one-component adhesive system according to the invention is used for the adhesive bonding and/or sealing of metals, glass and/or plastics materials.

Suitable metal substrates can generally be produced from all metals or metal alloys that are conventional in the field. Metals such as, for example, aluminium, stainless steel, steel, titanium, iron-containing metals and alloys are preferably used. The substrates that are to be bonded can additionally be composed of different metals.

The plastics substrates that are to be bonded are, for example, polycarbonates (PC), polyamides, polyvinyl chloride, polyurethanes, polyvinyl acetate, polyacrylates or polymethacrylates, polyethylene, polystyrene, polypropylene and/or polyesters, such as, for example, polybutylene terephthalate (PBT) and/or polyethylene terephthalate (PET).

The substrates can additionally be lacquered or printed.

The substrates that are to be bonded can further have any desired form necessary for the use of the resulting composite. In the simplest form, the substrates are planar. Three-dimensional substrates can, however, also be bonded using the reactive one-component adhesive system according to the invention.

Composite

There is likewise provided according to the invention a composite that is bonded by the reactive one-component adhesive system according to the invention, as defined above.

EXPERIMENTAL PART

The examples which follow serve to illustrate the present invention but are not to be interpreted as being a limitation of the scope of protection.

All percentages relate to weight, unless specified otherwise.

The NCO contents were determined titrimetrically in accordance with DIN EN ISO 11909.

OH numbers were determined titrimetrically in accordance with DIN 53240-2: 2007 November, and acid numbers were determined in accordance with DIN 3682 5. The indicated OH contents were calculated from the analytically determined OH numbers.

The residual monomer contents were measured in accordance with DIN EN ISO 10283 by gas chromatography with an internal standard.

The proportions of bisadduct and molecular weights were determined by gel permeation chromatography in accordance with DIN 55672-1 (Gel permeation chromatography (GPC)—Part 1: Tetrahydrofuran (THF) as eluant) against polystyrene standards, with the difference that a flow rate of 0.6 ml/min instead of 1.0 ml/min was used. The proportions of bisadduct in % by unit area taken from the chromatograms, which were determined with software assistance, were each equated approximately to proportions in wt. % and indicated as such, based on the total amount of mono- and bis-adduct.

All viscosity measurements were carried out using a Physica MCR 51 rheometer from Anton Paar Germany GmbH (DE) in accordance with DIN EN ISO 3219.

Synthesis of Silane-Modified Formamides having the Formula (Ia)

Example 1: N-(3-Trimethoxysilylpropyl)formamide 1075.8 g (6 mol) of 3-aminopropyltrimethoxysilane are placed at room temperature, under a nitrogen atmosphere, in a flask having a thermometer, a KPG stirrer, a reflux condenser and a dropping funnel. 378.6 g (6.3 mol) of methyl formate are added dropwise, with stirring, in such a manner that the temperature does not exceed 50° C. When the exothermic reaction has subsided, stirring is continued for 4 hours at room temperature, and then excess methyl formate and the resulting methyl alcohol are distilled off under reduced pressure (0.1 mbar at 50° C.). A colourless liquid having a viscosity of 11 mPa·s at 23° C. is obtained.

Example 2: N-(3-Methyldimethoxysilylpropyl)formamide 99.6 g (0.6 mol) of 3-aminopropylmethyldimethoxysilane are placed at room temperature, under a nitrogen atmosphere, in a flask having a thermometer, a KPG stirrer, a reflux condenser and a dropping funnel. 40.3 g (0.67 mol) of methyl formate are added dropwise, with stirring, in such a manner that the temperature does not exceed 50° C. When the exothermic reaction has subsided, stirring is continued for 4 hours at room temperature, and then excess methyl formate and the resulting methyl alcohol are distilled off under reduced pressure (0.1 mbar at 50° C.). A colourless liquid having a viscosity of 11 mPas at 23° C. is obtained.

Example 3: N-(3-Triethoxysilylpropyl)formamide 221.4 g (1 mop of 3-aminopropyl-triethoxysilane are placed at room temperature, under a nitrogen atmosphere, in a flask having a thermometer, a KPG stirrer, a reflux condenser and a dropping funnel. 77.8 g (1.05 mol) of ethyl formate are added dropwise, with stirring, in such a manner that the temperature does not exceed 50° C. When the exothermic reaction has subsided, stirring is continued for 4 hours at room temperature, and then excess ethyl formate and the resulting ethyl alcohol are distilled off under reduced pressure (0.1 mbar at 80° C.). A colourless liquid having a viscosity of 13 mPa·s at 23° C. is obtained.

Example 4: N-(3-Methyldiethoxysilylpropyl)formamide 497.9 g (2.6 mol) of 3-aminopropylmethyldiethoxysilane are placed at room temperature, under a nitrogen atmosphere, in a flask having a thermometer, a KPG stirrer, a reflux condenser and a dropping funnel. 212.1 g (2.8 mol) of ethyl formate are added dropwise, with stirring, in such a manner that the temperature does not exceed 50° C. When the exothermic reaction has subsided, stirring is continued for 4 hours at room temperature, and then excess ethyl formate and the resulting ethyl alcohol are distilled off under reduced pressure (0.1 mbar at 80° C.). A colourless liquid having a viscosity of 12 mPas at 23° C. is obtained.

Synthesis of Silane-Modified Compounds having the General Formula(I)

Example 5

672 g (4 mol) of HDI (1,6-hexamethylene diisocyanate) are placed at 80° C., under a nitrogen atmosphere, in a flask having a thermometer, a KPG stirrer, a reflux condenser and a dropping funnel. 207.1 g (1 mol) of N-(3-trimethoxysilylpropyl)formamide (from Example 1) are then metered in, with stirring, over a period of one hour. When the addition is complete, the batch is stirred at 80° C. until a constant isocyanate content (34.7 wt. %) is reached. The resulting reaction mixture is passed at a feed rate of 600 ml/h over a thin-film evaporator at a pressure of 0.03 mbar and a temperature of 130° C. in order to remove excess HDI. A colourless liquid having a viscosity of 103 mPa·s at 23° C., an isocyanate content of 10.36 wt. %, a free HDI content of 0.07 wt. % and a proportion of bis-adduct of 15.7% is obtained.

The main component of the obtained product corresponds to the formula (VI):

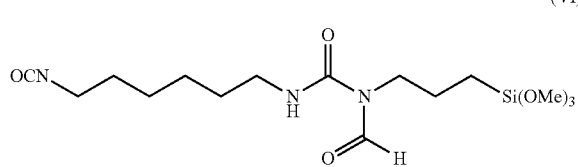

(VI)

Example 6: Comparison Example to Example 5

3150 g (18.75 mol) of HDI (1,6-hexamethylene diisocyanate) are placed at 80° C., under a nitrogen atmosphere, in a flask having a thermometer, a KPG stirrer, a reflux condenser and a dropping funnel. 448.2 g (2.5 mol) of 3-aminopropyltrimethoxysilane are than metered in, with stirring, over a period of one hour. Immediately after the addition of the first drop, the formation of a haze is to be observed, which increases in the course of the addition and agglomerates to form a solid. Constructive further processing of the batch as in Example 5 is not possible.

Example 7

1667.3 g (7.5 mol) of IPDI (isophorone diisocyanate) are placed at 80° C., under a nitrogen atmosphere, in a flask having a thermometer, a KPG stirrer, a reflux condenser and a dropping funnel. 207.1 g (1 mol) of N-(3-trimethoxysilyl-propyl)formamide (from Example 1) are then metered in, with stirring, over a period of one hour. When the addition is complete, the hatch is stirred at 80° C. until a constant isocyanate content (31.3 wt. %) is reached. The resulting reaction mixture is passed at a feed rate of 800 ml/h over a thin-film evaporator at a pressure of 0.02 mbar and a temperature of 140° C. in order to remove excess IPDI. A colourless liquid having a viscosity of 6900 mPa·s at 23° C., an isocyanate content of 9.9 wt. %, a free IPDI content of 0.32 wt. % and a proportion of bis-adduct of 10.3% is obtained.

Example 8

3960.0 g (22.5 mol) of TDI (2,4-toluene diisocyanate) are placed at 80° C., under a nitrogen atmosphere, in a flask having a thermometer, a KPG stirrer, a reflux condenser and a dropping funnel. 621.3 g (3 mol) of N-(3-trimethoxysilyl-propyl)formamide (from Example 1) are then metered in, with stirring, over a period of one hour. When the addition is complete, the batch is stirred at 80° C. until a constant isocyanate content (38.1 wt. %) is reached. The resulting reaction mixture is passed at a feed rate of 400 ml/h over a thin-film evaporator at a pressure of 0.02 mbar and a temperature of 140'C. in order to remove excess TDI. A yellowish liquid having a viscosity of 7080 mPa·s 23° C., isocyanate content of 11.6 wt. %, a free TDI content of 0.41 wt. % and a proportion of bis-adduct of 14.7% is obtained.

Synthesis of Silane-Modified Prepolymers Having the Formula (IV)

Example 9

262.5 g of castor oil and 13 mg of DBTL, are placed at 80° C., under a nitrogen atmosphere, in a flask having a thermometer, a KPG stirrer, a reflux condenser and a dropping funnel, and 307.3 g of the silane-modified formamide from Example 6 are added dropwise in such a manner that the reaction temperature does not exceed 90° C. When the addition is complete, the reaction mixture is stirred at 60° C. until a constant isocyanate content is reached (0.7 wt. %). The remaining isocyanate content is taken up by addition of methanol. The resulting binder is clear and has a viscosity of 13,500 mPa·s at 23'C.

For further processing, the binder is adjusted to a solids content of 50% with 1-methoxy-2-propyl acetate (MPA), and 0.25% Lupragen® N 700 (1,8-diazabicyclo-5,4,0-undec-7-ene) from BASF SE is added; the whole is applied with a knife in a layer thickness (wet) of 50 μm to glass plates. After a drying time of 4 hours at 23° C. and a relative humidity of 50%, the coating is touch-dry and after 4 days exhibits good solvent resistance to xylene, 1-methoxy-2-propyl acetate, ethyl acetate and acetone.

Example 10

92.8 g of Desmophen® A 160 SN (60% acrylic resin in solvent naphtha 100; hydroxyl content 2.7% on solid resin), Bayer Material Science AG, 67.3 g of 2-ethyl-1,3-hexanediol and 9 g of orthoformic acid triethyl ester are placed with 10 mg of DBTL at 80° C., under a nitrogen atmosphere, in a flask having a thermometer, a KPG stirrer, a reflux condenser and a dropping funnel, and 413.0 g of the silane formamide-HDI adduct (from Example 5) are added dropwise in such a manner that the reaction temperature does not exceed 90° C. When the addition is complete, the reaction mixture is stirred at 60° C. until no further isocyanate can be detected. The resulting binder is clear and has a viscosity of 230,000 mPas at 23° C.

For further processing, the binder is adjusted to a solids content of 50% with 1-methoxy-2-propyl acetate (MPA), and 0.25% Lupragen® N 700 (1,8-diazabicyclo-5,4,0-undec-7-ene) from BASF SE is added; the whole is applied with a knife in a layer thickness (wet) of 50 μm to glass plates. After a drying time of 4 hours at 23° C. and a relative humidity of 50%, the coating is touch-dry and after 4 days exhibits good solvent resistance to xylene, 1-methoxy-2-propyl acetate, ethyl acetate and acetone.

Example 11

1024 g (0.12 mol) of a polypropylene glycol (Acclaim Polyol 8200N; OH number 14 mg KOH/g) are placed with 50 mg of DBTL at 60° C., under a nitrogen atmosphere, in a flask having a thermometer, a KPG stirrer, a reflux condenser and a dropping funnel, and 109 g of the silane formamide-HDI adduct (from Example 5) are added dropwise in such a manner that the reaction temperature does not exceed 80° C., When the addition is complete, the reaction mixture is stirred at 60° C. until a constant isocyanate content is reached (0.05 wt. %). The remaining isocyanate content is taken up by addition of methanol and the reaction mass is stabilised by adding 100 mg of dibutyl phosphate and 2 g of vinyltrimethoxysilane as water acceptor. The resulting binder is clear and has a viscosity of 11,600 mPas at 23° C.

Example 12

950 g (0.1 mol) of a polypropylene glycol (Acclaim Polyol 18200N; OH number 6.5 rug KOH/g) are placed with 50 mg of DBTL at 60° C., under a nitrogen atmosphere, in a flask having a thermometer, a KPG stirrer, a reflux condenser and a dropping funnel, and 50 g of the silane formamide-HDI adduct (from Example 5) are added dropwise in such a manner that the reaction temperature does not exceed 80° C. When the addition is complete, the reaction mixture is stirred at 60° C. until a constant isocyanate content is reached (0.08 wt. %). The remaining isocyanate content is taken up by addition of methanol and the reaction mass is stabilised by adding 50 mg of dibutyl phosphate and 2 g of vinyltrimethoxysilane as water acceptor. The resulting binder is clear and has a viscosity of 75,700 mPas at 23° C.

Example 13

999 g (0.12 mol) of a polypropylene glycol (Acclaim® Polyol 8200N; OH number 14 mg KOH/g; Bayer Material Science AG) are placed with 60 mg of DBTL at 60° C., under a nitrogen atmosphere, in a flask having a thermometer, a KPG stirrer, a reflux condenser and a dropping funnel, and 101.0 g of the silane formamide-TDI adduct (from Example 8) are added dropwise in such a manner that the reaction temperature does not exceed 80° C. When the addition is complete, the reaction mixture is stirred at 60° C. until a constant isocyanate content is reached (0.02 wt. %). The remaining isocyanate content is taken up by addition of methanol and the reaction mass is stabilised by adding 60 mg of dibutyl phosphate and 2.2 g of vinyltrimethoxysilane as water acceptor. The resulting binder is clear and has a viscosity of 63,000 mPas at 23° C.

Application Examples for Adhesives and Sealing Materials

In order to assess the application properties of the different polymers, they were processed in the following formulation:

|  | Amount used in wt. % |
|---|---|
| Polymer | 31.34 |
| Filler (Socal $U_1S_2$) | 47.01 |
| Plasticiser (Jayflex DINP) | 18.80 |
| Drying agent (Dynasylan VTMO) | 1.88 |
| Adhesion promoter (Dynasylan 1146) | 0.94 |
| Catalyst (Lupragen N 700) | 0.03 |

In order to prepare the formulation, the filler (Socal® U1S2 from Solvay), the plasticiser (Jayflex™ DINP from Exxon) and the drying agent (Dynasylan® MAO from Evonik) are added to the binder, and mixing is carried out at 3000 rpm in a vacuum dissolver with a wall scraper. The adhesion promoter (Dynasylan® 1146 from Evonik) is then added and incorporated by stirring in the course of 5 minutes at 1000 rpm. Lastly, the catalyst (Lupragen® N700 from BASE SE) is stirred in at 1000 rpm, and the finished mixture is finally exposed to the air in vacuo.

In order to measure the physical properties, both membranes having a thickness of 2 mm and test specimens on a glass substrate are prepared in accordance with DIN EN ISO 11600. Testing of the Shore hardness was carried out on the membranes in accordance with DIN 53505. The modulus at 50% elongation is measured in accordance with DIN EN ISO 11600 at 23° C.

The following table shows the results that were obtained:

|  | Ex. 14 (polymer from Ex. 11) | Ex. 15 (polymer from Ex. 12) |
|---|---|---|
| Shore A hardness | 61 | 17 |
| 50% modulus [N/mm²] | 3.0 | 0.8 |
| Film drying time, 100 μm [min] | 45 | 30 |

The invention claimed is:

1. A compound of formula (I):

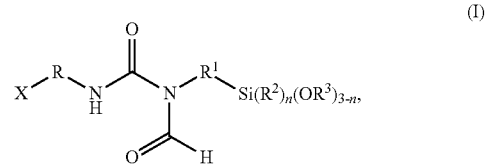

wherein:

X represents an optionally substituted, linear or branched, aliphatic, alicyclic, araliphatic, heterocyclic and/or aromatic structural unit having from 1 to 40 carbon atoms, wherein one or more non-adjacent methylene groups can each be replaced by O or S; or X represents —H or —NCO;

R represents an at least divalent, optionally substituted, linear or branched, aliphatic, alicyclic, araliphatic and/or aromatic structural unit having from 1 to 40 carbon atoms, wherein one or more non-adjacent methylene groups can each be replaced by O or S;

$R^1$ represents an at least divalent, optionally substituted, linear or branched, aliphatic, alicyclic, araliphatic and/or aromatic structural unit having from 1 to 12 carbon atoms, wherein one or more non-adjacent methylene groups can each be replaced by O or S;

$R^2$ and $R^3$ each independently of the other represents an optionally substituted, linear or branched, aliphatic group having from 1 to 12 carbon atoms; and n represents an integer from 0 to 2.

2. The compound according to claim 1, wherein $R^2$ and $R^3$ each independently of the other represents methyl or ethyl.

3. The compound according to claim 1, wherein R represents hexyl, $R^1$ represents propyl, $R^2$ and $R^3$ each independently of the other represents methyl or ethyl, and n represents an integer from 0 to 2.

4. The compound according to claim 1, which is represented by the following formula (III):

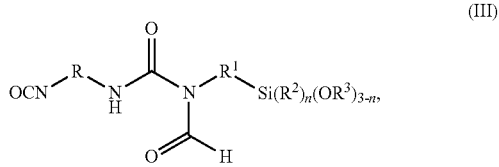

wherein R, $R^1$, $R^2$, $R^3$ and n are as defined in claim 1.

5. The compound according to claim 1, which is represented by the following formula (VI):

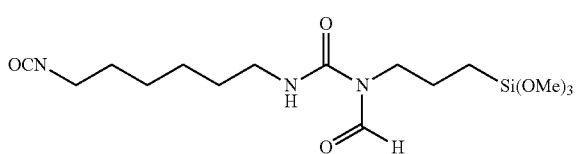

(VI)

6. A process for the preparation of the compound of formula (I) according to claim 1, comprising reacting a silane-modified formamide of formula (Ia) with an isocyanate of formula (Ib):

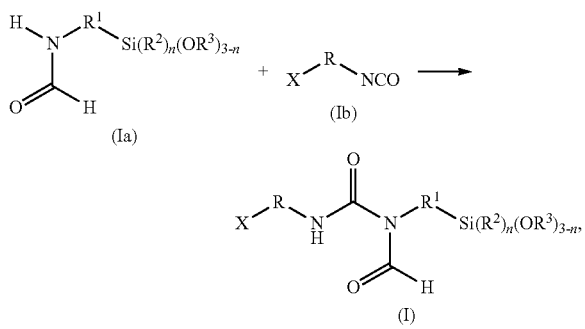

wherein X, R, $R^1$, $R^2$, $R^3$ and n are as defined in claim 1.

7. A method comprising utilizing the compound according to claim 1 for the preparation of a silane-modified compound of formula (IV):

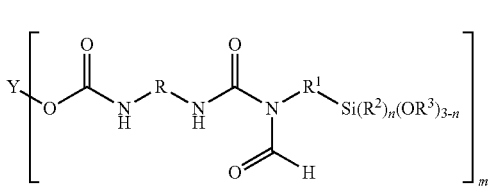

by reacting the compound of formula (I) wherein X represents an —NCO group with a compound of the formula $Y—(OH)_m$;
wherein R, $R_1$, $R^2$, $R^3$ and n are as defined in claim 1,
Y is an optionally substituted, linear or branched, aliphatic, alicyclic, araliphatic, heterocyclic and/or aromatic structural unit having from 1 to 40 carbon atoms or a structural unit reduced by m OH radicals of a polyhydric alcohol (polyol) or of a polyurethane, polyurea, polyester, polyether, polycarbonate, polyacetal, polyacrylate, polyester amide or polythioether polyol, and
m represents a number from 1 to 10.

8. A silane-modified compound of formula (IV):

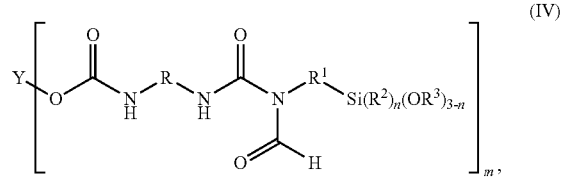

wherein
Y is an optionally substituted, linear or branched, aliphatic, alicyclic, araliphatic, heterocyclic and/or aromatic structural unit having from 1 to 40 carbon atoms or a structural unit reduced by m OH radicals of a polyhydric alcohol (polyol) or of a polyurethane, polyurea, polyester, polyether, polycarbonate, polyacetal, polyacrylate, polyester amide or polythioether polyol;
R represents an at least divalent, optionally substituted, linear or branched, aliphatic, alicyclic, araliphatic and/or aromatic structural unit having from 1 to 40 carbon atoms, wherein one or more non-adjacent methylene groups can each be replaced by O or S;
$R^1$ represents an at least divalent, optionally substituted, linear or branched, aliphatic, alicyclic, araliphatic and/or aromatic structural unit having from 1 to 12 carbon atoms, wherein one or more non-adjacent methylene groups can each be replaced by O or S;
$R^2$ and $R^3$ each independently of the other represents an optionally substituted, linear or branched, aliphatic group having from 1 to 12 carbon atoms; and
n represents an integer from 0 to 2, and
m represents a number from 1 to 10.

9. A process for the preparation of the silane-modified prepolymer of formula (IV) according to claim 8, comprising:
reacting a compound of formula (III) with a compound of the formula $Y—(OH)_m$:

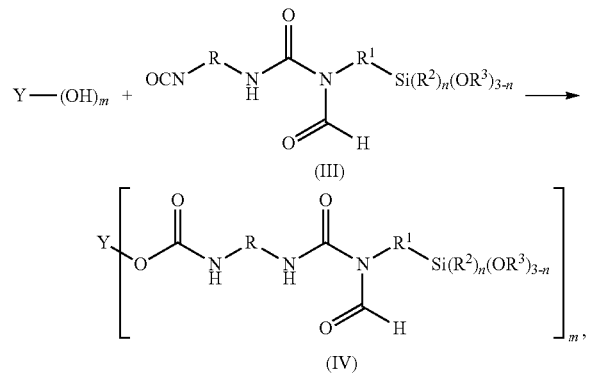

wherein R, $R^1$, $R^2$, $R^3$, n and m are as defined in claim 8.

10. A method comprising utilizing the compound according to claim 1 for the production of adhesives and sealing materials, lacquers, coatings, sizes, inks and/or printing inks.

11. A reactive one-component coating system comprising at least one compound according to claim 1.

12. A method comprising utilizing the reactive one-component coating system according to claim 11 for coating metal, wood, wood-based materials, glass, leather, textiles, plastics materials, mineral materials, cork, fibres, concrete, paper, cardboard or films.

13. A reactive one-component adhesive system comprising at least one compound according to claim 1.

14. A method comprising utilizing the reactive one-component adhesive system according to claim 13 for the adhesive bonding and/or sealing of metal, wood, wood-based materials, glass, leather, textiles, plastics materials, mineral materials, cork, fibres, concrete, paper, cardboard or films.

15. A kit comprising the reactive one-component adhesive system according to claim 13, for the adhesive bonding and/or sealing of metal, wood, wood-based materials, glass, leather, textiles, plastics materials, mineral materials, cork, fibres, concrete, paper, cardboard or films.

16. A composite comprising metal, wood, wood-based materials, glass, leather, textiles, plastics materials, mineral materials, cork, fibres, concrete, paper, cardboard or films adhesively bonded by the reactive one-component adhesive system according to claim 13.

* * * * *